United States Patent [19]

Le Suer

[11] 4,070,385
[45] Jan. 24, 1978

[54] PHOSPHORUS, NITROGEN AND SULFO-CONTAINING ADDITIVES

[75] Inventor: William Monroe Le Suer, Cleveland, Ohio

[73] Assignee: The Lubrizol Corporation, Wickliffe, Ohio

[21] Appl. No.: 777,880

[22] Filed: Mar. 15, 1977

Related U.S. Application Data

[60] Continuation-in-part of Ser. No. 634,390, Nov. 24, 1975, Pat. No. 4,026,812, which is a division of Ser. No. 424,246, Dec. 12, 1973, Pat. No. 3,926,821.

[51] Int. Cl.$^2$ .................. C07F 00/00; C07F 3/06; C07F 1/10; C07F 3/10
[52] U.S. Cl. .................. 260/429 R; 260/429 K; 260/429.9; 260/430; 260/431; 260/438.1; 260/439 R; 260/926; 260/938; 260/947
[58] Field of Search ............ 260/429 R, 429 K, 429.9, 260/430, 431, 438.1, 439 R, 926, 938, 947

[56] References Cited

U.S. PATENT DOCUMENTS

| | | | |
|---|---|---|---|
| 4,000,188 | 12/1976 | Dear et al. | 260/429 R |
| 4,014,926 | 3/1977 | Dear et al. | 260/429.9 |

*Primary Examiner*—Delbert E. Gantz
*Assistant Examiner*—Irving Vaughn
*Attorney, Agent, or Firm*—James W. Adams, Jr.; Daniel N. Hall

[57] ABSTRACT

Compositions made by reaction of (A) at least one phosphorus acid compound of the formula:

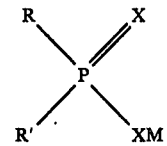

wherein each X is independently oxygen or divalent sulfur, M is hydrogen or an equivalent of metal or ammonium cation, R is a hydrogen atom or a hydrocarbyl or hydrocarbyloxy or hydrocarbyl mercapto group of about one to about thirty carbon atoms and R' is XM or R with the proviso that the total number of carbon atoms in both R and R' is at least two, with (B) at least one sulfo-containing compound of the formulae:

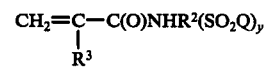

and

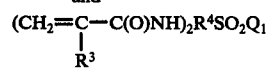

wherein $y$ is one or two, $R^3$ is hydrogen or lower alkyl group, $R^2$ is a divalent or trivalent hydrocarbyl group, $R^4$ is a trivalent hydrocarbyl group, and Q is —OH, —OR$^3$, —OM, an alkylene polyamine residue, or N(R$_3$)$_2$, are novel and useful and have utility as, for example, additives for water-containing hydraulic fluids.

28 Claims, No Drawings

PHOSPHORUS, NITROGEN AND SULFO-CONTAINING ADDITIVES

REFERENCE TO RELATED APPLICATIONS:

This application is a continuation-in-part of U.S. application Ser. No. 634,390 filed Nov. 24, 1975, now U.S. Pat. No. 4,026,812 which in turn is a division of Ser. No. 424,246 filed Dec. 12, 1973, now U.S. Pat. No. 3,926,821.

FIELD OF THE INVENTION

This invention relates to new compositions of matter and to lubricating and functional fluids containing them. More particularly, the compositions of this invention are made by the reaction of certain phosphorus acid compounds with certain sulfo-containing compounds. This invention also relates to lubricant and hydraulic fluid compositions containing these compositions as well as processes for preparing them.

BRIEF DESCRIPTION OF THE PRIOR ART

The use of sulfo-, nitrogen-, and phosphorus-containing compositions as additives for lubricants and functional fluids to improve one or more performance characteristics of such materials is well known. Among the functional fluids whose properties can be so improved are aqueous hydraulic fluids. Some hydraulic fluids are based on mixtures of glycol, water and oil, while others are based on oil-water emulsions. Regardless of their specific type, these aqueous hydraulic fluids are particularly useful in areas where fire resistance is of prime concern, such as on ships, in steel mills, etc. It is desirable to impart extreme pressure properties to such aqueous hydraulic fluids and it is an advantage of this invention that through its practice this can be done.

Further general background on the use of aqueous hydraulic fluids, their properties and compositions can be found in "Lubrication" Vol. 48, 161 (1962) published by *Texaco Inc.* of N.Y., N.Y., which is expressly incorporated herein for its background information and discussion of aqueous hydraulic fluids.

It is known that various types of phosphorus acids can be reacted with unsaturated carboxylic acid derivatives such as acrylamides and nitrato compounds (see for example, U.S. Pat. Nos. 2,709,156; 2,742,431; 2,766,208; and 3,098,824). It has also been disclosed in U.S. Pat. No. 4,000,188 that mercaptans can be added to alkylene-amidoalkane sulfonic acid salts such as are disclosed hereinbelow. It has not been previously known or suggested, however, that phosphorus acid compounds can be reacted with sulfo-, nitrogen-containing olefinic compounds to produce the additive compositions of this invention or to incorporate those additive compositions in lubricant and functional fluid compositions such as those of the present invention.

SUMMARY OF THE INVENTION

A novel class of phosphorus-, sulfo-, and nitrogen-containing products which are useful as additives for lubricants and functional fluids, particularly aqueous hydraulic fluids, has been found. These additives are made by reacting certain phosphorus acid compounds with sulfo- and nitrogen-containing olefinic substrates. Aqueous hydraulic fluid compositions prepared by combining these additives with glycol-water and oil-water emulsion fluids are within the scope of this invention.

DETAILED DESCRIPTION OF THE INVENTION

The phosphorus acid compounds, (A) used as addends in making the compositions of the present invention are of the formula:

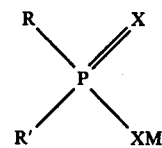

wherein each X is independently oxygen or divalent sulfur, M is hydrogen or an equivalent of a metal or ammonium cation, R is hydrogen or a hydrocarbyl, hydrocarbyloxy or hydrocarbyl mercapto group of about one to about thirty carbons atoms and R' is XM or R, with the proviso that the total number of carbon atoms in both R and R' is at least two. Preferably each X is oxygen and each R and R' contains between one and eighteen carbon atoms and is substantially aliphatic in nature; more preferably both R and R' are independently $C_{1-18}$ alkoxy groups and each X is a divalent sulfur atom.

When reference in this specification and the appended claims is made to hydrocarbyl, hydrocarbyloxy, hydrocarbyl mercapto, aliphatic or alkyl groups, it is to be understood, unless expressly stated to the contrary, that reference is also being made to substantially hydrocarbyl, substantially hydrocarbyloxy, substantially hydrocarbyl mercapto, substantially aliphatic, and substantially alkyl groups. The description of these groups as being substantially hydrocarbyl means that they contain no non-hydrocarbyl substituents which would significantly affect the principal hydrocarbyl characteristics or properties of the group relevant to their uses as described herein. Thus, it is obvious, for example, in the context of this invention, that a purely hydrocarbyl $C_{20}$ alkyl group and a $C_{20}$ alkyl group substituted with a methyl mercapto or methoxyl substituent at a point in the chain remote from other polar (i.e., non-hydrocarbyl) groups, would be substantially similar in their properties with regard to its use in this invention, and would in fact be recognized as art equivalents by those of ordinary skill in the art. That is, one of ordinary skill in the art would recognize both such groups to be substantially hydrocarbyl, etc.

Non-limiting examples of substituents which do not significantly alter the hydrocarbyl, etc., properties or nature of hydrocarbyl, etc., groups of this invention are the following:

Ether groups (especially hydrocarbyloxy and particularly alkoxy groups of up to ten carbon atoms)

Amino groups (including mono- and disubstituted aminos such as mono- and dialkyl amino or mono- and diaryl amino and the like, e.g., ethyl amino, dimethyl amino, diheptyl amino, cyclohexyl amino, benzyl amino, etc.)

Oxo groups

such as in ketones and aldehydes)

Oxa groups (e.g., —O— linkages in the main carbon chain)
Nitro groups
Imino groups

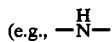

linkages in the main carbon chain)
Cyano groups
Fluoro groups
Chloro groups
Thioether groups (especially $C_{1-10}$ alkyl thioether )
Thia groups (e.g., —S— linkages in the main carbon chain)
Carbohydrocarbyloxy groups

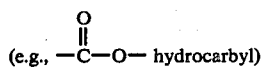

Sulfonyl groups
Sulfinyl groups

This list is intended to be merely illustrative and not exhaustive and the omission of a certain class of substituent is not meant to require its exclusion.

In general, if such substituents are present, it will be found that not more than two for each ten carbon atoms in the hydrocarbyl group and preferably not more than one for each ten carbon atoms, will not substantially affect the hydrocarbyl nature of the group. Nevertheless, the hydrocarbyl, hydrocarbyloxy, hydrocarbyl mercapto, etc., groups usually will be free from non-hydrocarbon groups due to economic considerations.

In the above formula, R and R′ can be saturated or unsaturated and include alkyl, cycloalkyl, aryl, arylalkyl, alkylaryl, cycloalkenyl, etc. Suitable specific groups include methyl, ethyl, n-propyl, isopropyl, n-butyl, isobutyl, amyl, isoamyl, n-hexyl, 2-ethylhexyl, 4-methyl-2-pentyl, cyclohexyl, chlorocyclohexyl, methylcyclohexyl, heptyl, n-octyl, tertiary octyl, nonyl, lauryl, cetyl, phenyl, bromophenyl, 2,4-dichlorophenylethyl, chlorophenyl, nitrophenyl, methoxyphenyl, ethylphenyl, propylphenyl, butyphenyl, benzylphenylethyl, octenyl, cyclohexenyl, ethyl cyclopentyl, N,N′-dibutylamino propyl phenyl, 3-nitro octyl, p-carbothoxy phenyl, phenoxyphenyl, naphthyl, alkylated naphthyl such as propylene tetramer-substituted naphthyl, acetyl phenyl, 2-ethoxyethyl, 6-ethyl amino heptyl, 4-cyanophenyl, 3,3,3-trifluoropropyl, dichloromethyl 3-thia-n-octyl, 2-methyl mercapto naphthyl, 4-ethyl sulfonyl-n-butyl, 4-phenylsulfinyl phenyl, etc.

Methods of the preparation of such phosphorus acid compounds are well known to those of skill in the art and need not be repeated here. For convenience, however, reference is made to "Organo-Phosphorus Compounds", by G. M. Kosolapoff, John Wiley Publishers, 1950, New York, which is incorporated herein by reference for its disclosure of methods for preparing these phosphorus acid compounds.

A particularly preferred type of phosphorus acid compound which may be used in this invention is prepared by the reaction of phosphorus pentasulfide or homologs thereof (e.g., $P_4S_{10}$) with hydroxy compounds which contain the organic groups R and R′ as defined above. An example of this type of reaction is the reaction of phosphorus pentasulfide with ethyl alcohol to produce, 0,0-diethyl phosphorodithioic acid.

Metal or ammonium salts of the above phosphorus acids can be prepared quite conveniently by neutralization techniques well known to those of skill in the art, such as treating the particular acid with a metal oxide, metal or ammonium hydroxide. Thus, for example, the calcium salt of the afore-described 0,0-diethyl phosphorodithioic acid can be prepared by reacting the acid with calcium oxide. Similarly, the tetramethyl ammonium salt can be prepared by reaction of the same acid with tetramethyl ammonium hydroxide.

As noted above, M represents one equivalent of a metal or ammonium cation. Such metal cations are derived from Groups I(A), I(B), II(A), II(B), III(A), and VIII of the periodic table. When M represents an ammonium cation, it can also be represented as $N^+(R^3)_4$, ($R^3$ being defined below), that is a monoammonium salt.

The sulfo- and nitrogen-containing compounds, (B), used in the preparation of the compositions of this invention are of the general formulae:

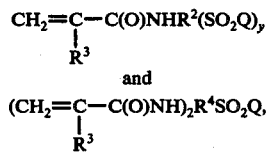

wherein $y$ is one or two, each $R^3$ is independently hydrogen or a lower alkyl group of one to seven carbons, $R^2$ is a di-or trivalent hydrocarbyl group having one to eighteen carbon atoms, $R^4$ is a trivalent hydrocarbyl group having one to eighteen carbon atoms, and Q is selected from the group consisting of —OH, —OR³, —OM, —O(Alkylene-O)$_n$—R³, —N(R³)$_2$,

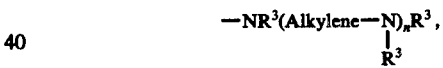

—ON$^{-+}$(R³)$_4$, and

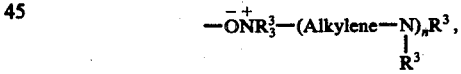

wherein $n$ has an average value of about one to about ten, and the alkylene group has from one to ten carbon atoms.

When $R^2$ is a divalent hydrocarbyl group the following illustrate some of the groups within the scope of this invention (where a named group has several isomeric forms (e.g., butylene), all such forms are included):

| | |
|---|---|
| Methylene | 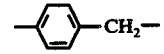 |
| Ethylene | Cyclohexylene |
| Propylene | Cyclopentylene |
| Butylene | Methylcyclopentylene |
| Hexylene | |
| |  |
| Octylene | |
| | 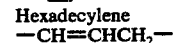 |
| Decylene | Hexadecylene |
| —CH=CH— | —CH=CHCH$_2$— |

-continued

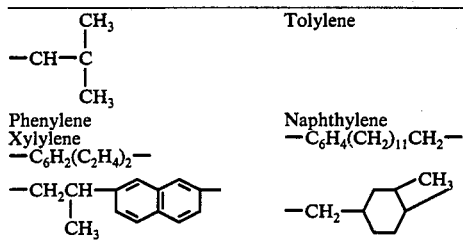

Trivalent radicals such as $R^2$ and $R^4$ are similar to the above but have an additional hydrogen atom abstracted.

Many obvious variations of these radicals will be apparent to those of skill in the art and are included within the scope of the invention.

Preferably, Q is —OH or —OM that is, one equivalent of a cation derived from a Group I(A), I(B), II(A), II(B), III(A) or VIII metal or amine or polyamine.

Often it is preferred that the Q be derived by neutralization from an alkylene polyamine of the formula:

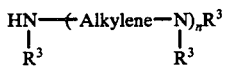

wherein $n$ has an average value between about one and about ten and the alkylene group is a lower alkylene group of one to ten carbon atoms. As noted above, $R^3$ is an aliphatic or hydroxy-substituted aliphatic group of up to about seven carbon atoms; often the alkylene group contains between two and about six carbon atoms.

Such alkylene polyamines include methylene polyamines, ethylene polyamines, butylene polyamines, propylene polyamines, pentylene polyamines, etc. The higher homologs and related heterocyclic amines such as piperazines and N-amino alkyl substituted piperazines are also included. Specific examples of such polyamines are ethylene diamine, triethylene, tetramine, tris-(2-aminoethyl)amine, propylene diamine, trimethylene diamine, tripropylene tetramine, tetraethylene pentamine, heptaethylene hexamine, etc.

Higher homologs obtained by condensing two or more of the above-noted alkylene amines are similarly useful as are mixtures of two or more of the afore-described polyamines.

Ethylene polyamines, such as some of those mentioned above, are especially useful for reasons of cost and effectiveness. Such polyamines are described in detail under the heading Ethylene Amines in Kirk Othmer's "Encyclopedia of Chemical Technology", 2d Edition, Vol. 7, pages 22–37, Interscience Publishers, New York (1965). Such polyamines are most conveniently prepared by the reaction of ethylene dichloride with ammonia or by reaction of an ethylene imine with a ring opening reagent such as water, ammonia, etc. These reactions result in the production of a complex mixture of polyalkylene polyamines including cyclic condensation products such as the afore-described piperazines. Ethylene polyamine mixtures are particularly useful in preparing the compositions of this invention due to reasons of economy and availability. On the other hand, quite satisfactory products can also be obtained by the use of the pure polyamines themselves.

The sulfo-products derived from the amines and polyamines described above can be ammonium salts, dehydrated derivatives of such salts and mixtures thereof, depending on the reaction conditions used to prepare them. Variation of the reaction conditions to produce the desired type of product is well within the skill of the ordinary worker in the art. When the sulfo-product is an ammonium salt, it can be represented by the above formula in which

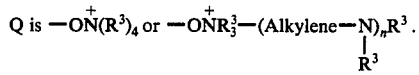

As noted above, Q in the formula of the sulfo-nitrogen-containing compound of this invention can be —$OR^3$ or $O\text{-(Alkylene-O)}_n R^3$. Such compounds are, of course, esters of the corresponding monohydric (e.g., $HOR^3$) and polyhydric (e.g., $HO\text{—(Alkylene-O)}_n R^3$) alcohols. They can be prepared by a variety of techniques known to those of skill in the art, such as esterification (with or without conventinal esterification catalyst), ester exchange, reaction with epoxides, etc. Usually esters will be prepared by heating a sulfonic acid with a monohydric alcohol, polyhydric alcohol, etc. Generally, the esters will be derived from monohydric alcohols of 1 to 7 carbon atoms such as methanol, ethanol, isopropanol, tertiary butanol, etc., or from polyhydric alcohols such as ethylene glycol, diethylene glycol, 2-methoxy ethanol, tri(1,2-propylene) glycol and the like.

Preferably $R^3$ is hydrogen or methyl group, while $R^2$ is a lower alkene or aryl group (e.g., phenyl, tolyl, etc). Most preferably, $R^2$ in the above formula, is a lower alkylene group of up to 10 carbon atoms, such as ethylene, propylene, methyl propylene, etc. When $R^2$ is such a lower alkylene group, it can be represented as —$(R^3)_2CCH_2$— wherein each $R^3$ is independently as hereinbefore defined and the sulfo group is attached directly to the unsubstituted methylene carbon atoms.

Specific non-limiting examples of the sulfo-nitrogen-containing olefinic compounds useful in preparing the compositions of the present invention are illustrated by the following (for convenience only the acid form is shown, since derivation of the corresponding esters, salts, etc., is well within the skill of those of skill in the art):

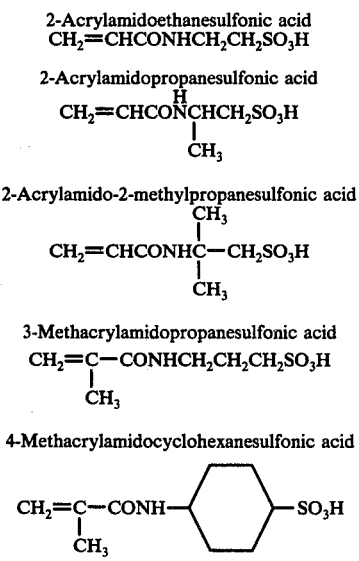

-continued
2-Acrylamido-2-phenylethanesulfonic acid

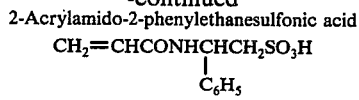

Specific examples of related olefinic sulfonyl- and nitrogen-containing substrates wherein $R^2$ is a trivalent group, are the following (again, only the acid form is shown for convenience):

1-(Acrylamido)-3,4-phenyl disulfonic acid

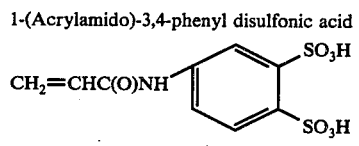

2-(Methacrylamido)-1,4-butane disulfonic acid

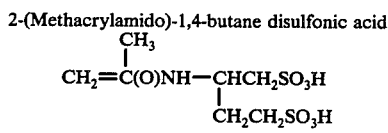

1-(Acrylamido)-4,5-naphthalene disulfonic acid

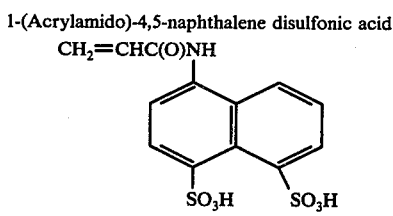

Related olefinic sulfonyl- and nitrogen-containing compounds wherein $R^4$ is a trivalent group, are the following:

1,1-bis(acrylamido)-2-methylpropane-2-sulfonic acid

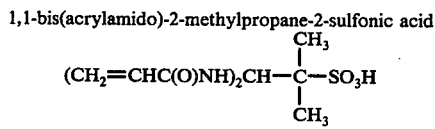

1,1-bis(methacrylamido)-2-ethyldecane-2-sulfonic acid

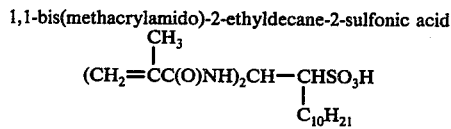

1,2-bis(acrylamido)-4-phenylsulfonic acid

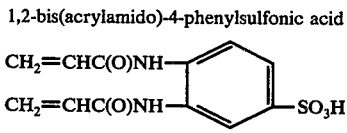

The sulfo- and nitrogen-containing compounds used in the preparation of the additives of this invention are available from a number of sources known to those of skill in the art. For example, a particularly preferred substrate wherein $R^2$ is an alkylene group is available from the reaction of acryl chloride with an appropriate amino sulfonic acid. Alternatively, similar compounds can be produced by the reaction of an aliphatic nitrile with a 1-olefin in the presence of a sulfating agent comprised of a mixture of sulfuric acid and acid anhydride (e.g., $SO_3$) containing at least two moles of acidic anhydride per mole of sulfuric acid. One such reaction is represented by the general equation:

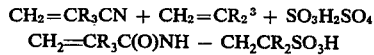

Further details about such reactions can be found in Canadian Pat. No. 704,778 and U.S. Pat. Nos. 3,506,707 and 3,544,597, which are hereby incorporated by reference for their relevant disclosures.

Another class of preferred sulfonyl- and nitrogen-containing substrates has two acryl olefinic bonds and a trivalent $R^4$ group is conveniently prepared by the reaction of an aldehyde having at least one alphahydrogen substituent (i.e., a hydrogen substituent on the carbon atom adjacent to the carbonyl bonded carbon atom), a nitrile and a sulfonating agent. Preferably, the sulfonating agent is sulfur-trioxide, fuming sulfuric acid or sulfuric acid such as 98%, 96%, or 90% aqueous sulfuric acid. Chlorosulfonic acid or other well-known sulfonating agents can also be used. Further details of this type of preparation are to be found in U.S. Pat. No. 3,531,442 which is hereby incorporated by reference for its relevant disclosures.

Generally, formation of the novel compositions of this invention is achieved by contacting about 0.1 to about 1.0 moles of at least one of the afore-described phosphorus acid compounds with about 1 to about 0.1 equivalent of at least one of the aforedescribed sulfo-, nitrogen-containing compounds (1 equivalent of the latter is the molecular weight of the sulfo compound divided by the number of terminal olefinic linkages present). The reaction normally is carried out for a period of 0.1 to 24, generally, 0.1 to 12 hours, at a temperature of about 15° C up to the decomposition point of any component of the reaction mixture, preferably from 50° C to 200° C.

Suitable substantially inert organic liquid solvents or diluents may be used in the reaction and include such relatively low boiling liquids as hexane, heptane, benzene, toluene, xylene, methanol, isopropanol, etc., as well as high boiling materials such as solvent neutral oils, bright stocks and various types of synthetic and natural lubricating oil base stocks. Factors governing the choice and use of such materials are well known to those of skill in the art. Normally such a diluent will be used to facilitate heat control, handling, filtration, etc. It is often desirable to select a diluent which will be compatible with the other materials, which are to be present in the environment where the product is intended to be used.

The inventive compositions can be removed from such solvent/diluents by such standard procedures as distillation, evaporation, precipitation, crystallization, dialysis, etc., when desired. Alternatively, if the solvent/diluent is, for example, a base oil suitable for use in the functional fluid compositions of this invention, the product can be left in the solvent/diluent and used to form the lubricating or functional fluid composition as described below.

While it is possible to contact the phosphorus acid compounds and olefinic sulfo-, nitrogen-containing compounds in any order, it is preferable to add the acid compound to the sulfo-, nitrogen-containing compound in an appropriate solvent/diluent. It is also preferable, but not essential, to use an alkali or alkaline earth metal salt of the phosphorus acid as the phosphorus acid compound.

The sulfo-, nitrogen-containing reaction products corresponding to the compositions of this invention can be represented by the following formulae wherein the —X— atom is attached to either the carbon alpha or beta to the amido group:

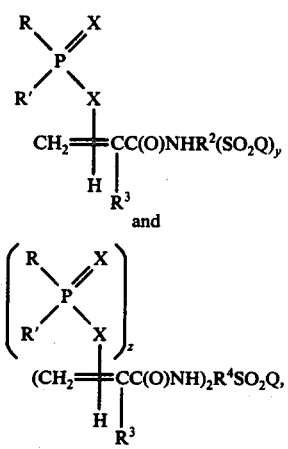

wherein $z$ is one or two, and R, R', $R^2$, $R^3$, $R^4$, X, Q, and $y$ have the meanings ascribed to them in the above description of the phosphorus acid and sulfo-nitrogen compounds of this invention. The compositions of this invention include mixtures of two or more different reaction products represented by the above formulae.

Naturally, the preferences set forth in the afore-going descriptions can be incorporated into analogous formula. For example, a preferred composition of this invention can be represented by the formula:

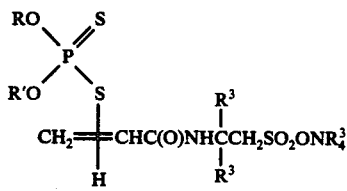

wherein R and R' are $C_{1-10}$ alkyl groups and each $R^3$ is independently hydrogen or an aliphatic hydrocarbyl group, preferably alkyl, of one to seven carbons.

EXAMPLES

The following non-limiting examples are specific preferred embodiments of the present invention. All references to percentages, parts, etc., in the present specification and appended claims refer to percentages, parts, etc., by weight unless expressly stated otherwise.

EXAMPLE 1

A mixture of 414 parts of 2-acrylamido-2-methylpropane-1 sulfonic acid and 600 parts of isopropanol at reflux temperature (85° C) is slowly added over a 5 hour period to 1,648 parts of a 50 percent toluene solution of sodium diisooctyl phosphorodithioate. Heating is continued for an additional hour and the mixture stirred at room temperature for eighteen hours. Then 1,238 parts of diluent oil is added and the mixture stripped to 110° C/3mm. Filtration with the aid of 40 grams of filter aid provides an oil solution of the desired product which is characterized by a sulfur content of 6.56%, a phosphorus content of 2.58% and a sodium content of 1.85%.

EXAMPLE 2

To a mixture of 704 parts of di(4-methyl secondary amyl) phosphorodithioic acid in 200 parts of methyl amyl alcohol is slowly added over seven hours at 80°-85° C, 414 parts of 2-acrylamido-2-methylpropanesulfonic acid. After heating for a period of 10 hours at 80°-90° C., the mixture is filtered through cloth and neutralized with 25% caustic liquid soda to a pH of 7. Stripping to 90° C/19mm provides the desired product which is characterized by a sulfur content of 16.88%, a phosphorus content of 5.06%, a nitrogen content of 2.56% and a sodium content of 5.70%

EXAMPLE 3

A phosphorodithioic dialkyl acid is prepared by reacting $P_2S_5$ (1 mole) with 4 moles of a commercial mixture of synthetic mixture of coco alcohols having a carbon chain length ranging between 14 and 18 carbons. The resulting acid is characterized by a phosphorus content of 0.93% and a sulfur content of 10.01%. This acid is converted into a calcium salt by treatment of 2150 parts of acid with 353 parts of calcium hydroxide. The calcium salt is characterized by a phosphorus content of 3.34% and a sulfur content of 6.58%.

To 158 parts of the afore-described calcium salt at 80° C is slowly added 68 parts of 2-acrylamido-1-octadecane sulfonic acid over 0.5 hour. The mixture is held at 85°-90° C. for 5 hours and blown with nitrogen at a rate of 0.25scfh (standard cubic feet per hour). The final product is obtained as a filtrate by filtration with the aid of 7 parts of filter aid at a temperature of below 90° C. and is characterized by a sulfur content of 6.57%, a nitrogen content of 0.96% and a phosphorus content of 2.29%.

EXAMPLE 4

To 151 parts of di(isooctyl) phosphorodithioic acid under a nitrogen atmosphere is added over 0.5 hour at 80° C, parts of 2-acrylamido-2-methylpropanesulfonic acid. To this mixture is added 150 parts of isopropyl alcohol. The mixture is held at reflux for 5 hours while being sparged with nitrogen at 0.25scfh. The reaction mixture is stored for eighteen hours at room temperature and is stripped to 70° C/30mm over a period of 1.5 hours. Filtration with the aid of filter aid at a temperature under 90° C provides the desired product as a white, waxy solid being characterized by a sulfur content of 15.83%, a nitrogen content of 2.10% and a phosphorus content of 5.45%.

EXAMPLE 5

To 1600 parts of a barium salt of the phosphorodithioic dialkyl ester acid described in Example 3 at 80° C. is added 300 parts of 2-acrylamido-2-methylpropanesulfonic acid over a period of 0.25 hour. Reaction mixture is held at 80°-85° C. for 8 hours while being blown with nitrogen at a rate of 1 to 2scfh. Stripping over a four hour period to 90° C/30mm and filtration with the aid of 30 parts of filter aid provides the desired product as a clear yellow liquid characterized by a sulfur content of 6.85%, a nitrogen content of 1.06% and a phosphorus content of 2.43%.

EXAMPLE 6

A solution of 423 parts of O,O-di(2-ethylhexyl)phosphoromonothioic acid in 500cc parts by volume of petroleum naphtha is added to an oil solution of 292 parts of the potassium salt of 2-acrylamido-2-phenylethanesulfonic acid. The resulting mixture is stirred for two hours at 25°-=° C. and then stripped to 130° C/0.5mm to yield the desired product as a residue.

EXAMPLE 7

A mixture of 250 parts of diphenylphosphinic acid and an equal volume of diluent oil is added over a two hour period to a mixture of 278 parts of 1,1-bis-(acrylamido)2-ethylpropyl-2-sulfonic acid and 500 parts of diluent oil. After stirring for 2 hours at 30° C, anhydrous ammonia is added to the reaction mixture in an amount sufficient to neutralize all the sulfonic acid groups. Cooling and the addition of pentane to the mixture precipitates the ammonium salt of the desired product. This precipitate is collected on a filter, washed with pentane and then dried at 45°-55° C. in vacuo to provide the final product.

EXAMPLE 8

One mole of the phosphorus acid compound described in Example 1 is added to a mixture of 0.5 mole of 1,2-bis(acrylamido)-4-phenylsulfonic acid calcium salt and an equal volume of isopropanol. Reaction mixture is then stirred for 4 hours and stripped to 120° C/5mm to provide the final product as a residue.

EXAMPLE 9

A mixture of 0.25 mole of the phosphorus acid compound described in Example 3 and three volumes of isopropanol is added to 0.25 mole of 1-acrylamido-4,5-naphthalene disulfonic acid zinc salt suspended in 500ml of isopropanol over a period of two hours. The reaction mixture is then stirred at 40°-60° C. and stripped to 100° C/10mm to provide the final product as a residue.

EXAMPLE 10

The product of Example 3 was treated with a commercial mixture of ethylene polyamine corresponding in stoichiometry to tetraethylene pentamine to form the corresponding ammonium salt as the desired product.

In one embodiment of this invention the products of the reaction of the phosphorus compound with the sulfo-, nitrogen-containing compounds are further reacted with a polyoxyalkylene glycol or epoxide to form an ester of a glycol or polyoxyalkylene glycol. Suitable polyethers are ethylene glycol, diethylene glycol, dipropylene glycol, tri(1,2-butylene)glycol, etc., including glycols containing up to thirty carbon atoms. Suitable epoxides which yield similar products include those having about two to about twenty carbon atoms and are exemplified by the following: ethylene oxide, propylene oxide, ethylene chlorohydrin, styrene oxide, butyl epoxy stearate, 1-tetradecane oxide, 1-octadecane oxide, etc. Lower alkylene oxides (i.e., those containing less than eight carbon atoms) are preferred. Sulfur analogs of the abovedescribed epoxides (i.e., that is, thioepoxides or thiiranes) can also be used alone or in admixture with the above-described epoxides or glycols to form the corresponding thioanalogs of these esters.

Preferred gylcols are those containing divalent ethylene or 1,2-propylene group such as ethylene glycol, 1,2-propylene glycol, di-, tri-, tetra-, penta-, hexa-, etc. (oxyethylene)glycol, and the like.

Preferred epoxides are those which can be represented by the formula:

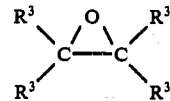

wherein each $R^3$ is independently hydrogen or a $C_{1-7}$ lower alkyl group. Typical of such epoxides are ethylene oxide, propylene oxide, 1,2- and 2,3-butylene oxide and the like. Substituted epoxide such as epichlorohydrin can also be used.

Usually at least one mole of glycol or epoxide per equivalent of sulfonic acid are used. Naturally, larger amounts of epoxide can be used if it is desired to form poly(oxyalkylene)esters. Such reactions may be carried out at temperatures between about 0° C. up to the decomposition temperature of the reaction mixture or one of its components, normally between about 15° and about 150° C. In epoxide reactions cooling may be necessary to keep the reaction temperature within these ranges.

EXAMPLE 11

One mole of the product described in Example 1 in an oil diluent was reacted with 5 moles of ethylene oxide to produce an ester of penta(oxyethylene)glycol.

EXAMPLES 12 and 13

In the same manner as described in Example 11, propylene oxide and butylene thioepoxide were reacted with the products of Examples 2 and 3, respectively, to form the desired products.

As is noted above, the compositions of this invention are particularly useful in water-oil emulsions which are to be used as fire-resistant hydraulic fluids. Generally, these emulsions are of the oil-in-water type where water is the continuous phase and oil the dispersed phase. However, the compositions may also be employed advantageously in water-in-oil emulsions. The oils in these emulsions can be hydrocarbon oil having a viscosity from about 40 SUS (Saybolt University Seconds) at 100° to 500 SUS at 210° F. Mineral oils having lubricating viscosities (e.g., SAE 10 to 90, preferably SAE 50 to 90, grade oils according to the standards set forth by the Society of Automotive Engineers) are especially advantageous for use in such emulsions. Mixtures of oils from different sources are similarly useful. Such mixtures are available from mineral oils, vegetable oils, animal oils, synthetic oils of the silicone type, synthetic oils of the polyolefin type, synthetic oils of the polyester type, and so forth.

The oil-water emulsion compositions of this invention comprise from 1 to 80 parts water, from about 20 to about 99 parts of oil and from about 0.1 to about 20, preferably about 0.5 to about 15 parts of at least one composition according to this invention. Preferred emulsions having extremely desirable properties are composed of from 30 to 50 parts water and from 50 to 70 parts oil, and the above-noted amount of inventive additive. Emulsions intended specifically for use as fire-resistent hydraulic fluids should contain at least 30% water.

These emulsions can be prepared by simply mixing water, oil, an emulsifier (such as those described below), and the additives of this invention (and any other ingredients which are known in the art to be desirable) in an homogenizer or any other efficient blending device.

Heating the emulsion during or after its preparation is not necessary, though it may be preferred. The order of mixing the above-described ingredients is not critical although it is often convenient to first prepare a concentrate comprising about 40 to about 95 parts of the various additives (such as the inventive additives) and from about 60 to about 5 parts of a substantially inert liquid diluent or solvent and then emulsifying the concentrate with water in the appropriate proportions. Usually the diluent or solvent will be oil which is compatible with the oil to be used in the final emulsion but other diluents and solvents can be used.

Although the oil-water hydraulic fluid compositions of this invention described above are in themselves useful in many instances, they are nevertheless susceptible to improvement by the incorporation of various other types of chemical additives, which impart the properties desired for specific applications. Emulsifiers such as the succinic acid esters described in U.S. Pat. No. 3,281,356 are often helpful in forming the emulsions (the U.S. Pat. No. 2,281,356 patent is hereby incorporated by reference for its relevant disclosures in this regard). Emulsion stabilizers which function to improve the stability of the emulsion against the deterioration due to temperature, pressure, oxidation of the oil, and other harmful environments, are another type of useful additives. Among such stabilizers are the phosphatides which are also described in detail in the aforementioned U.S. Pat. No. 3,281,356 at column 11. This disclosure is hereby incorporated by reference for its relevant details. A particularly useful phosphatide is soybean lecithin which is described in detail in "Encyclopedia of Chemical Technology", Kirk Othmer, Vol. 8, pages 309–326 (1952).

Other types of emulsion stabilizers have also been used, such as aliphatic glycols, monoethers, and fatty acid esters of such glycols, alkali and ammonium salts of sulfonic acids, neutral alkali metal salts of fatty acids and other materials known to those of the art. A detailed description of such materials is given in the aforementioned U.S. Pat. No. 3,281,356, which is hereby incorporated by reference in its entirety for its relevant disclosures.

When a stabilizer is used in the oil-water compositions of this invention, only a small amount is needed. It can be as little as about 0.01 part and seldom exceeds about two parts per hundred parts of the total emulsion. In many instances, it is within the range of about 0.1 to about 1 part per hundred parts of emulsion.

While the compositions of the present invention are incorporated in the lubricating and hydraulic compositions of the invention as extreme pressure, anti-wear and load-carrying agents, it may sometimes be desirable to incorporate one or more additional agents to supplement their action. Such supplemental agents may be illustrated by the lead, nickel or Group IIA and IIB metal phosphorodithioate salts in which the metal may be magnesium, calcium, barium, strontium, zinc, cadmium, lead or nickel. Zinc phosphorodithioates are particularly preferred. Other types of extreme pressure agents which can find use in the lubricating oil compositions of this invention include chlorinated waxes, sulfurized or phosphosulfurized fatty acid esters, di- or trihydrocarbyl phosphites and phosphates, dihydrocarbon polysulfides and metal dithiocarbamates. These and other useful extreme pressure agents are described in more detail in the books both entitled "Lubricant additives" by Smith and Smalheer (Published by the Lezius-Hiles Co., of Cleveland, Ohio) and by M. W. Raney (Published by the Noyes Data Corporation of Park Ridge, New Jersey) pages 146–212, both of which are incorporated herein by reference for their disclosure of additional extreme pressure agents which can be used in conjunction with the additives of the present invention.

Still another type of additive which can be useful in the lubricating oil compositions of the present invention is rust-inhibiting agents. One or more rust-inhibiting agents can be used. The most effective rust-inhibiting agents in the water-oil emulsions of this invention are aliphatic amines, especially aliphatic primary amines having at least eight carbon atoms in the molecule. Preferably, such amines are tertiary alkyl primary amines and have at the most thirty carbon atoms in the molecules. Other conventional rust-inhibiting agents can also be used, either alone or in combination with the amines discussed above.

Other conventional types of rust-inhibiting agents are salts or aromatic acids, such as benzoic acid, etc., with the afore-described amines. Hydroxy alkyl amines, particularly those with long chains, (i.e., $C_8$–$C_{30}$ aliphatic amines) containing one or two hydroxy alkyl substituents on the nitrogen atom are also useful as rust-inhibiting agents in the lubricating oil compositions of this invention. Nitric acid salts of long-chained aliphatic amines such as those disclosed above are similarly useful.

The concentration of rust-inhibiting agent in the lubricating oil compositions and particularly the oil-water emulsions of this invention depend to some extent upon the relative concentration of water in the emulsion. Ordinarily from about 0.1 part to 2 parts of rust-inhibiting agent per hundred parts of emulsion is sufficient.

The oil-water emulsions of this invention may also contain a conventional foam inhibitor such as a commercial dialkyl siloxane polymer or polymer of a methacrylate. Freezing point depressants (i.e., water-soluble polyhydric alcohols such as glycerol or other polar substances such as the methyl ether of diethylene glycol) are also useful. The concentration of these additives is usally less than five parts per hundred parts of the oil-water emulsion.

Bacteriocides can also be included in the emulsions of this invention. These are illustrated by the nitrobromo alkenes such as 3-nitro-1-propylbromide, nitrohydroxy-alkanes, such as tri(hydroxymethyl)nitromethane, 2-nitro-2-ethyl-1,3-propanediol and 2-nitro-1-butanol and boric acid esters such as glycerol borate. The concentration of such bacteriocides usually range between about 0.001 to about 1 part per hundred parts of the oil-in-water emulsion.

Oxidation inhibitors can also be included in the lubricating oil compositions of this invention. Hindered phenols such as 2,4-di-t-butyl-6-methyl phenol, 4,4'-methylene(2,6-di-t-phenol), and 2,6-di-t-octyl-4-secondary butyl phenol, are representative of useful oxidation inhibitors. The concentration of such oxidation inhibitors in the lubricating oil compositions of this invention is usually between about 0.01 to about 2 parts per hundred parts of emulsion.

The following examples are illustrative of concentrates and oil-in-water emulsion compositions of the present invention.

Example 14 (emulsion)

| Component | Parts by Weight |
| --- | --- |
| Emulsifier* | 9.0 |
| Soybean Lecithin | 1.8 |
| Tertiary alkyl primary amine having a mol wt of 191 in which the tertiary alkyl radical is a mixture of radicals having 11 to 14 carbon atoms. | 0.6 |
| Product of Example 1 | 5.0 |
| SAE 40 mineral lubricating oil | 284.0 |
| Silicone anti-foam agent | 0.0075 |
| Water | |

*Emulsifier made by reacting a polyisobutenyl succinic anhydride with (isobutenyl group = $M_n$ 1000) with polyoxyethylene sorbitan monooleate.

Example 15 (concentrate)

| Component | Parts by Weight |
| --- | --- |
| Emulsifier of Example 14 | 9.0 |
| Soybean lecithin | 1.8 |
| Tertiary alkyl primary amine having a molecular weight of 330 in which the tertiary alkyl radical is a mixture of radicals having 18 to 24 carbon atoms. | 0.6 |
| Lead diamyl dithiocarbamate | 3.0 |
| Product of Example 3 | 3.0 |
| SAE 20 mineral lubricating oil | 282.0 |
| Silicone anti-foam agent | 0.0045 |

Example 16

| Component | Parts by Weight |
| --- | --- |
| Emulsifier of Example 14 | 18.0 |
| Soybean Lecithin | 3.6 |
| Nitric acid salt of the tertiary alkyl primary amine of Example 14 | 1.2 |
| Product of Example 2 | 18.0 |
| 4-methyl-2,6-di-t-butyl phenol | 3.0 |
| SAE 5 mineral lubricating oil | 534.0 |
| Silicone anti-foam agents | 0.015 |
| Water | 400.0 |

Example 17

| Component | Parts by Weight |
| --- | --- |
| The emulsifier of Example 14 | 45.0 |
| The product of Example 2 | 18.7 |
| Soybean lecithin | 9.0 |
| Tertiary alkyl primary amine of Example 14 | 3.0 |
| SAE 40 mineral lubricating oil | 24.3 |
| Silicone anti-foam agent | 0.022 |

Example 18

| Component | Parts by Weight |
| --- | --- |
| The product of Example 17 | 6.0 |
| SAE 40 mineral lubricating oil | 94.0 |

As noted above, the lubricant compositions of this invention can also be based on water-glycol mixtures. Such compositions usually comprise water as solvent and flame retarder, a water-soluble organic polymer thickener such as polyoxyethylene polymer or an acrylated methacrylate ester polymer, a water-miscible freezing point depressant, and small amounts of such additives as the afore-described anti-rust agents, oxidation inhibitors, and so on, as well as the additive compositions of this invention. The water-miscible freezing point depressant is usually a common glycol or glycol ether having from about 2 to 14 carbon atoms such as ethylene glycol diethylene glycol, triethylene glycol, ethylene glycol ethers, such as ethyl, methyl, propyl and butyl ethers thereof and similar ethers of diethylene glycol and triethylene glycol. In general, it is preferred to use simpler compounds such as represented by ethylene glycol, propylene glycol, butylene glycol, and diethylene glycol for they are cheap, easily obtainable and blend readily with water to give very low freezing point mixtures which form the good basis for hydraulic fluid compositions.

Usually, the water content of such water-glycol mixtures is limited to a maximum of about 45 percent to be free from freezing problems. The minimum amount of water is usually 10 percent also to avoid excessively high freezing points of the composition.

The preferred thickeners for use in these compositions are soluble organic polymeric compounds usually copolymers of ethylene oxide and 1,2-propylene or 1,3-propylene oxide. A preferred one is one containing about 75 mole percent ethylene oxide and about 25 mole percent of propylene oxide, copolymerized to a thick fluid polymer having a number average molecular weight of about and not in excess of 15,000 to 20,000. Such polymers have viscosities of about 50,000 to about 100,000 SUS at 100° F. Blends of such polymers may be used to achieve specific purposes. All of the fore-described additives which are used in the water-oil based hydraulic fluids can be used in appropriate circumstances in the water-glycol fluids. Usually solubility and compatibility dictate the choice of such additives which is within the skill of those skilled in the art.

The water-glycol based compositions of this invention contain 0.5 to 20 parts of the compositions of the invention per hundred parts of the total mixture in addition to the glycol-water thickener and other noted additives.

Exemplary of the water-glycol based compositions of this invention are the following:

EXAMPLE 19

A mixture of equal weights of water and ethylene glycol is prepared containing as a thickener a copolymer of ethylene oxide and 1,2-propylene oxide of number average molecular weight 15,000 having a viscosity of 50,000 SUS at 100° F, and 3 parts per hundred parts of water-glycol base of the product of Example 1.

EXAMPLE 20

A mixture of 33 parts by weight water and 67 parts be weight ethylene glycol is prepared and treated with one part by weight per hundred parts of the copolymer of Example 19 and five parts by weight of the product of Example 3.

While the compositions of this invention find particular use in the afore-described water-oil and water-glycol hydraulic fluids, they may also be used in lubricating compositions containing only natural or synthetic oils. Such usage is particularly favored when the additive composition is relatively non-polar, that is, it is an ester rather than a salt of free acid.

The compositions of this invention can be effectively employed in a variety of lubricating compositions based on diverse oils of lubricating viscosity such as natural or synthetic lubricating oil, or suitable mixtures thereof. The lubricating compositions contemplated include principally crankcase lubricating oils for spark-ignited and compression-ignited internal combustion engines including automobile and truck engines, two-cycle engine lubricants, aviation piston engines, marine and railroad diesel engines, and the like. However, automatic transmission fluids, tranaxle lubricants, gear lubricants, metal-working lubricants, hydraulic fluids, and other lubricating oil and grease compositions can benefit from the incorporation of the present composition.

Natural oils include animal oils and vegetable oils (e.g., casto oil, lard oil) as well as solvent-refined or acid-refined mineral lubricating oils of the paraffinic, naphthenic or mixed paraffinic-naphthenic types. Oils of lubricating viscosity derived from coal or shale are also useful base oils. Synthetic lubricating oils include hydrocarbon oils and halo-substituted hydrocarbon oils such as polymerized and interpolymerized olefins (e.g., polybutylene, polypropylenes, propylene isobutylene copolymers, chlorinated polybutylenes, etc.); alkyl benzenes (e.g., dodecylbenzenes, tetradecylbenzenes, dinonylbenzenes, di-(2-ethylhexyl)benzenes, etc.); polyphenyls (e.g., biphenyls, terphenyls, etc.); and the like. Alkylene oxide polymers and interpolymers and derivatives thereof where the terminal hydroxyl groups have been modified by esterification, etherification, etc., constitute another class of known synthetic lubricating oils. These are exemplified by the oils prepared through polymerization of ethylene oxide or propylene oxide, the alkyl and aryl ethers of these polyoxyalkylene polymers (e.g., methyl polyisopropyleneglycol ether having an average molecular weight of 1000, diphenyl ether of polyethylene glycol having a molecular weight of 500-1000, diethyl ether of polypropylene glycol having a molecular weight of 1000-1500, etc.) or mono- and polycarboxylic esters thereof, for example, the acetic acid esters, mixed $C_3$-$C_8$ fatty acid esters, or the $C_{13}$ Oxo acid diester of tetraethylene glycol. Another suitable class of synthetic lubricating oils comprises the esters of dicarboxylic acids (e.g., phthalic acid, succinic acid, maleic acid, azelaic acid, suberic acid, sebacic acid, fumaric acid, adipic acid, linoleic acid dimer, etc.) with a variety of alcohols (e.g., butyl alcohol, hexyl alcohol, dodecyl alcohol, 2-ethylhexyl alcohol, pentaerythritol, etc.). Specific examples of these esters include dibutyl adipate, di(2-ethylhexyl)sebacate, di-n-hexyl furmarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethyl-hexanoic acid, and the like. Silicon-based oils such as the polyakyl-, polyarly-, polyalkoxy-, or polyaryloxy-siloxane oils and silicate oils comprise another useful class of synthetic lubricants (e.g., tetraethyl silicate, tetraisopropyl silicate, tetra-(2-ethylhexyl)silicate, tetra-(4-methyl-2-tetraethyl)silicate, tetra-(p-tert-butylphenyl) silicate, hexyl-(4-methyl-2-pentoxy)-disiloxane, poly(methyl) siloxanes, poly(methylphenyl)-siloxanes, etc.). Other synthetic lubricating oils include liquid esters of phosphrous-containing acids (e.g., tricresyl phosphate, trioctyl phosphate, diethyl ester of decane phosphonic acid, etc.), polymeric tetrahydrofurans, and the like.

The lubricating oil compositions of this invention comprise a major amount of oil and a minor, load-carrying improving amount of at least one additive compositiion of the invention. Generally, this amount will be about 0.5 to about 20 parts additive per hundred parts oil.

Exemplary of these lubricating oil compositions are the following:

EXAMPLE 21

A mixture of 95 parts of SAE 40 oil and 5 parts of the additive composition of EXAMPLE 10.

EXAMPLE 22

A mixture of 90 parts of SAE 10W/30 oil, 7 parts of the additive composition of Example 3 and 3 parts of 2,4-di-t-butyl-6-methyl phenol in an antioxidant.

As indicated above during the description of the oil-water emulsions of this invention, it is often convenient to form concentrates of the additive compositions of this invention prior to incorporation of the additives in an emulsion composition. Such concentrates comprise about 40 to about 95 parts additive and about 60 to about 5 parts of substantially inert organic liquid diluents or solvents and are equally useful in preparing the lubricating oil composition of this invention. Analogous glycol-based concentrates comprising about 50 to about 95 parts additive composition and about 50 to about 5 parts of at least one glycol or glycol-ether are equally useful. Remarks made hereinbefore in regard to concentrates are applicable here.

What is claimed is:

1. A sulfur-, nitrogen- and phosphorus-containing composition made by reacting one or more phosphorus acid compounds of the formula

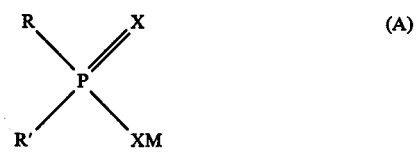

wherein each X is independently oxygen or divalent sulfur, M is a hydrogen, an equivalent of a metal of ammonium cation, R is hydrogen or a hydrocarbyl, hydrocarbyloxy, or hydrocarbyl mercapto group of about one to about thirty carbon atoms, and R' is XM or R, with the proviso that the total number of carbon atoms in both R and R' is at least two, with (B) one or more sulfo- and nitrogen-containing compounds of the general formulae:

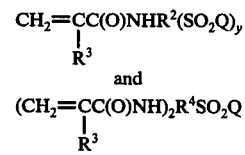

wherein $y$ is one or two, each $R^3$ is independently hydrogen or lower alkyl group of one to seven carbon atoms, $R^2$ is di- or trivalent hydrocarbyl group having one to eighteen carbon atoms, $R^4$ is a trivalent hydrocarbyl group having one to eighteen carbon atoms, and Q is selected from the group consisting of —OH —$OR^3$, —OM, —O(Alkylene-O)$_n$—$R^3$, —N($R^3$)$_2$, —$NR^3$(Alkylene-$NR^3$)$_n R^3$, —OH($R^3$)$_4$, and —$ONR_3{}^3$-(AlkyleneN$R^3$)$_n R^3$, wherein n has an average value of about one to about ten, M is as defined in (A) and te alkylene group has from one to ten carbon atoms.

2. A sulfo-, nitrogen- and phosphorus-containing composition selected from those corresponding to the formulae:

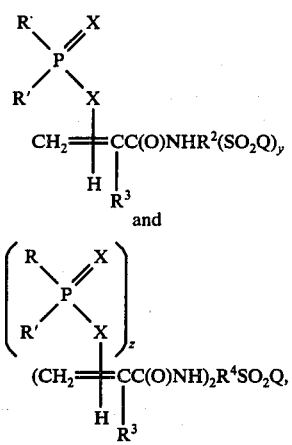

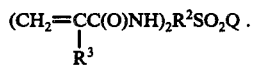

and mixtures of two or more such additives wherein z is one or two, R, R', $R^2$, $R^3$, $R^4$, X, Q and y are set forth in claim 1.

3. The composition of claim 1 wherein R' is the same as R and R is a hydrocarbyloxy group containing one to about eighteen carbon atoms and each X is oxygen.

4. The composition of claim 2 wherein R' is the same as R and R is a hydrocarbyloxy group containing one to about eighteen carbon atoms and each X is oxygen.

5. The composition of claim 1 wherein each X is a divalent sulfur atom and R and R' are independently $C_1$-$C_{18}$ alkoxy groups.

6. The composition of claim 1 wherein (B) is of the general formula

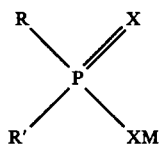

7. The composition of claim 1 wherein M is hydrogen, a Group I, II(A), II(B) metal cation or mixtures thereof.

8. The composition of claim 1 wherein Q is selected from the group consisting of —$NR^3$(Alkylene-$NR^3$)$_n$$R^3$ and —$ONR_3^3$—(Akylene-$NR^3$)$_n$$R^3$ and mixtures thereof.

9. The composition of claim 2 wherein Q is selected from the group consisting of —$NR^3$(Alkylene-$NR^3$)$_n$$R^3$ and —$ONR_3^3$—(Alkylene-$NR^3$)$_n$$R^3$ and mixtures thereof.

10. The composition of claim 1 wherein Q is —O(Alkylene—O)$_n$$R^3$.

11. The composition of claim 2 wherein Q is —O(Alkylene—O)$_n$$R^3$.

12. A process for preparing a sulfur-, nitrogen- and phosphorous-containing composition which comprises reacting one or more phosphorus compounds of the formula

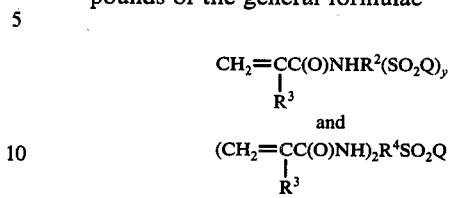

wherein each X is independently oxygen or divalent sulfur, M is a hydrogen, an equivalent of a metal or ammonium cation, R is hydrogen or a hydrocarbyl, hydrocarbyloxy, or hydrocarbyl mercapto group of about one to about 30 carbon atoms, and R' is XM or R, with the proviso that the total number of carbon atoms in both R and R' is at least two, with B. one or more sulfo- and nitrogen-containing compounds of the general formulae $$CH_2=CC(O)NHR^2(SO_2Q)_y$$
$$|$$
$$R^3$$

and $$(CH_2=CC(O)NH)_2R^4SO_2Q$$
$$|$$
$$R^3$$

wherein y is one or two, each $R^3$ is independently hydrogen or lower alkyl group of one to seven carbon atoms, $R^2$ is di- or trivalent hydrocarbyl group having one to eighteen carbon atoms, $R^4$ is a trivalent hydrocarbyl group having one to eighteen carbon atoms, and Q is selected from the group consisting of —OH, —$OR^3$, —OM, —O(Alkylene-O)$_n$—$R^3$, —N($R^3$)$_2$, —$NR^3$(Alkylene-$NR^3$)$_n$$R^3$, —OH($R^3$)$_4$, and -$ONR_3^3$-(Alkylene-$NR^3$)$_n$$R^3$, wherein n has an average value of about one to about ten, M is as defined in (A) and the alkylene group has from one to ten carbon atoms.

13. The process of claim 12 wherein R' is the same as R and R is a hydrocarbyloxy group containing one to about eighteen carbon atoms and each X is oxygen.

14. The process of claim 12 wherein each X is a divalent sulfur atoms and R and R' are independently $C_1$-$C_{18}$ alkoxy groups.

15. The process of claim 12 wherein Q is selected from the group consisting of M, wherein M is a Group I, II(A), or II(B) metal cation and $ONR_3^3$—(Alkylene $NR^3$)$_n$$R^3$.

16. The composition of claim 1 wherein R' is the same as R and R is a hydrocarbyloxy group containing one to about eighteen carbon atoms and each X is a divalent sulfur atom.

17. The composition of claim 2 wherein R' is the same as R and R is a hydrocarbyloxy group containing one to about 18 carbon atoms and each X is a divalent sulfur atom.

18. The composition of claim 1 wherein (B) is of the general formula

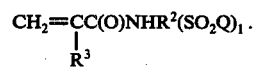

19. The composition of claim 18 wherein R' is the same as R and R is a hydrocarbyloxy group containing one to about eighteen carbon atoms.

20. The composition of claim 18 wherein each X is a divalent sulfur atom.

21. The composition of claim 2 corresponding to one or more compounds of the general formula.

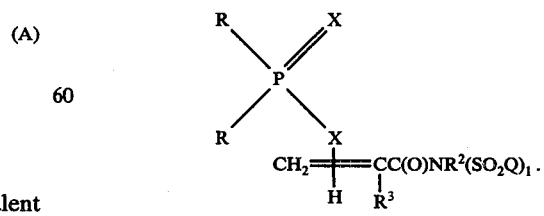

22. The composition of claim 21 wherein R' is the same as R and R is a hydrocarbyloxy group containing one to about eighteen carbon atoms.

23. The composition of claim 22 wherein each X is a divalent sulfur atom.

24. The composition of claim 1 wherein M is selected from the group consisting of hydrogen, lithium, sodium, potassium, magnesium, calcium, brium, and mixtures thereof.

25. The composition of claim 2 wherein R is hydrogen, a Group I, II(A), II(B) metal cation, or mixtures thereof.

26. The composition of claim 18 wherein M is a Group I, II(A), II(B) metal cation or mixtures thereof.

27. The composition of claim 21 wherein M is hydrogen, a Group I, II(A), II(B) metal cation or mixtures thereof.

28. The composition of claim 1 wherein Q is —OM and M of Q is selected from the group consisting of hydrogen, Group I, II(A), II(B) metal cations, $NH^+_4$ and mixtures thereof.

* * * * *